(12) United States Patent
Konawa et al.

(10) Patent No.: US 11,510,828 B2
(45) Date of Patent: Nov. 29, 2022

(54) ABSORBENT ARTICLE

(71) Applicant: DAIO PAPER CORPORATION, Ehime (JP)

(72) Inventors: Satoko Konawa, Tochigi (JP); Yoko Suzuki, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 791 days.

(21) Appl. No.: 16/305,217

(22) PCT Filed: Jun. 12, 2017

(86) PCT No.: PCT/JP2017/021592
§ 371 (c)(1),
(2) Date: Nov. 28, 2018

(87) PCT Pub. No.: WO2017/217356
PCT Pub. Date: Dec. 21, 2017

(65) Prior Publication Data
US 2020/0121523 A1 Apr. 23, 2020

(30) Foreign Application Priority Data
Jun. 14, 2016 (JP) .............................. JP2016-118172

(51) Int. Cl.
*A61F 13/533* (2006.01)
*A61F 13/00* (2006.01)
(Continued)

(52) U.S. Cl.
CPC ...... *A61F 13/533* (2013.01); *A61F 13/00017* (2013.01); *A61F 13/4756* (2013.01); *A61F 13/51108* (2013.01)

(58) Field of Classification Search
CPC .............. A61F 13/533; A61F 13/51108; A61F 13/532; A61F 13/4756; A61F 13/00017; A61F 13/51104; A61F 2013/51078
See application file for complete search history.

(56) References Cited

U.S. PATENT DOCUMENTS

| 2011/0251575 | A1 | 10/2011 | Kuroda et al. | |
|---|---|---|---|---|
| 2011/0288514 | A1* | 11/2011 | Kuroda | ............... A61F 13/4756 604/380 |
| 2013/0085464 | A1* | 4/2013 | Kudo | ............... A61F 13/15731 604/380 |

FOREIGN PATENT DOCUMENTS

| EP | 2380541 | 10/2011 |
|---|---|---|
| EP | 2612635 | 7/2013 |

(Continued)

OTHER PUBLICATIONS

International Search Report for PCT/JP2017/021592 dated Jul. 11, 2017.

(Continued)

*Primary Examiner* — Jessica Arble
(74) *Attorney, Agent, or Firm* — IPUSA, PLLC

(57) ABSTRACT

(Object) To prevent a high compression portion from being defectively formed and also a top sheet from being torn. (Means of Achieving the Object) A sanitary napkin (1) in which a low compression portion (15) and a high compression portion (16, 17, 18) are formed on a bottom surface of a compressed groove (10) that is recessed from a skin contact surface side. The high compression portion includes regularly-arranged high compression portions (16) that are regularly arranged in a longitudinal direction of the compressed groove (10), a large-area high compression portion (17) that is irregularly arranged in the compressed groove (10) and has an area larger than an area of each of the regularly-arranged high compression portions (16), and an (Continued)

auxiliary high compression portion (18) that is arranged at one side, in a longitudinal direction of the napkin, of the large-area high compression portion (17) through the low compression portion (15) so as to surround the one side, in the longitudinal direction of the napkin, of the large-area high compression portion (17).

7 Claims, 5 Drawing Sheets

(51) Int. Cl.
*A61F 13/475* (2006.01)
*A61F 13/511* (2006.01)

(56) References Cited

FOREIGN PATENT DOCUMENTS

| | | |
|---|---|---|
| JP | 2004-008596 | 1/2004 |
| JP | 2010-148706 | 7/2010 |
| JP | 2014-147461 | 8/2014 |
| JP | 2016-059540 | 4/2016 |
| WO | 2012/105533 | 8/2012 |
| WO | 2015/072502 | 5/2015 |

OTHER PUBLICATIONS

Extended European Search Report for 17813252.8 dated Feb. 28, 2019.

\* cited by examiner

ABSORBENT ARTICLE

TECHNICAL FIELD

The present invention generally relates to an absorbent article used for a sanitary napkin, a panty liner, an incontinence pad, or toiletry, and specifically relates to an absorbent article in which a low compression portion and a high compression portion are formed on the bottom surface of a compressed groove that is recessed from a skin contact surface side.

BACKGROUND ART

Conventionally, as absorbent articles such as a panty liner, a sanitary napkin, and an incontinence pad, an absorbent article that includes an absorbent body made of cotton-like pulp and interposed between a liquid impermeable back sheet such as a polyethylene sheet or a polyethylene-sheet-laminated non-woven fabric and a liquid permeable top sheet such as a non-woven fabric or a liquid permeable plastic sheet is known.

Various improvements have been made to this type of absorbent article. Currently, there is a technique that forms various forms of compressed portions that are concaved from a skin contact surface side toward a non-skin side, such that leakage of body fluids can be prevented and also the absorbent article can be readily deformed along the body shape when the absorbent article is worn.

For example, Patent Document 1 below discloses an apparatus for manufacturing an absorbent article. The apparatus includes an embossing roll having projecting portions for forming a compressed groove, and the embossing roll includes tension suppressing portions for suppressing tension that is applied to a top sheet when forming a compressed groove. On the surface of the embossing roll, the suppressing portions are provided around the projecting portions located next to each other in a roll axial direction. The tension suppressing portions are raised from the surface of the embossing roll up to a position lower than low pressure portions of the projecting portions for forming a compressed groove. According to the manufacturing apparatus, because the tension suppressing portions raised lower than the low pressure portions are provided, and a level difference between the tension suppressing portions and the low pressure portions is small, it is possible to reduce tension applied in the roll axial direction of the top sheet. Accordingly, in a manufactured absorbent article, effects of the top sheet and the absorbent body being sufficiently integrally compressed, and of a compressed groove being less likely to be defectively formed, are described.

Further, Patent Document 2 discloses an absorbent article in which a compressed groove is composed of high-compressed portions and low-compressed portions. The high-compressed portions include approximately transverse high-compressed portions that are formed so as to approximately traverse the compressed groove in the width direction and that are arranged at intervals in a longitudinal direction of the compressed groove, and also include non-transverse high-compressed portions that are formed so as not to traverse the compressed groove and that are arranged at intervals in a region between the approximately transverse high-compressed portions.

RELATED-ART DOCUMENTS

Patent Documents

[Patent Document 1] Japanese Unexamined Patent Application Publication No. 2016-59540

[Patent Document 2] Japanese Unexamined Patent Application Publication No. 2010-148706

SUMMARY OF THE INVENTION

Problem to be Solved by the Invention

However, in the manufacturing apparatus disclosed in Patent Document 1, the tension suppressing portions press the surface of an absorbent article in the vicinity of front and back sides of a compressed groove. Thus, traces of the tension suppressing portions pressing the surface may be left in the vicinity of the front and back sides of the compressed groove, which may cause the fit and appearance of the absorbent article to decrease. Also, in a region other than the front and back sides of the compressed groove, no countermeasure is taken against tension that causes the top sheet to stretch when pressure is applied. Thus, the compressed groove readily becomes defectively formed or the top sheet readily becomes torn.

In the above absorbent article disclosed in Patent Document 2, the compressed groove has the approximately transverse high-compressed portions having a relatively larger area and the non-transverse high-compressed portions having a relatively smaller area. When the approximately transverse high-compressed portions having a larger area are formed, large pressure is applied over a wide range, thereby causing a high compression pattern to be unsuccessfully formed and resulting in poor appearance. Alternatively, there is also a problem in that large pressure may be applied only in part, causing the top sheet to be torn.

In view of the above, it is a general object of the present invention to provide an absorbent article in which a low compression portion and a high compression portion are formed on the bottom surface of a compressed groove, and that is capable of preventing the high compression portion from being defectively formed and also preventing the top sheet from being torn.

Means to Solve the Problem

In order to solve the above problem, the invention according to claim 1 provides an absorbent article including an absorbent body interposed between a liquid permeable top sheet and a liquid impermeable back sheet, a low compression portion and a high compression portion being formed on a bottom surface of a compressed groove that is recessed from a skin contact surface side, wherein the high compression portion includes regularly-arranged high compression portions that are regularly arranged in a longitudinal direction of the compressed groove, a large-area high compression portion that is irregularly arranged in the compressed groove and has an area larger than an area of each of the regularly-arranged high compression portions, and an auxiliary high compression portion that is arranged at one side, in a longitudinal direction of the absorbent article, of the large-area high compression portion through the low compression portion so as to surround the one side, in the longitudinal direction of the absorbent article, of the large-area high compression portion.

According to the invention of claim 1, in the aim of exhibiting an effect of causing a center portion of the absorbent body in the width direction to protrude toward a skin side when pressure is exerted from both sides in the width direction when a sanitary napkin is worn, and also in the aim of improving appearance of the compressed groove, the large-area high compression portion having a relatively larger area is irregularly arranged at a predetermined position of the compressed groove. The auxiliary high compression portion wider than the large-area high compression portion is arranged at one side, in the longitudinal direction of the absorbent article, of the large-area high compression portion through the low compression portion so as to surround the one side of the large-area high compression portion. The one side in the longitudinal direction of the absorbent article is regarded as a downstream side of the direction in which the line moves when the absorbent article is manufactured. Accordingly, in embossing roll processing, the large-area high compression portion can be pressed while the absorbent body including the top sheet is being temporarily held by the auxiliary high compression portions. Accordingly, it becomes possible to reduce a possibility of the large-area high compression portion being defectively formed and improve appearance of the high compression portion, while also preventing the top sheet from being torn.

The invention according to claim 2 provides the absorbent article according to claim 1, wherein the large-area high compression portion is formed in a vastly enlarged portion in which a width of the compressed groove is vastly enlarged.

In the invention according to claim 2, the large-area high compression portion is arranged in the vastly enlarged portion in which the width of the compressed groove is vastly enlarged. Thus, the vastly enlarged portion serves as a base for transmitting pressure, which is exerted from the both sides in the width direction when the sanitary napkin is worn, to the center portion in the width direction. This allows the center portion of the absorbent body in the width direction to readily protrude toward the skin side, and also allows appearance of the compressed groove to improve.

The invention according to claim 3 provides the absorbent article according to claim 1 or 2, wherein an auxiliary low compression portion that is wider than the auxiliary high compression portion is disposed so as to surround one side, in the longitudinal direction of the absorbent article, of the auxiliary high compression portion.

In the invention according to claim 3, the auxiliary high compression portion is disposed at the one side of the large-area high compression portion, and also the auxiliary low compression portion is disposed at the one side, in the longitudinal direction of the absorbent article, of the auxiliary high compression portion. Thus, in the process of pressing the compressed groove, while the absorbent body including the top sheet is being temporarily held by the auxiliary low compression portion at pressure lower than that for the auxiliary high compression portion, the high compression portion can be pressed. Accordingly, it becomes possible to further improve appearance of the high compression portion while also securely preventing the top sheet from being torn.

The invention according to claim 4 provides the absorbent article according to any one of claims 1 to 3, wherein a shape of the auxiliary high compression portion in planar view is approximately same as or different from a shape of the one side, in the longitudinal direction of the absorbent article, of the large-area high compression portion.

In the invention according to claim 4, by forming the shape of the auxiliary high compression portion in planar view approximately the same as the shape of the one side, in the longitudinal direction of the absorbent article, of the large-area high compression portion, an effect of temporarily holding down the top sheet can be improved. Also, in order to suppress wrinkles due to the auxiliary high compression portion being formed, the auxiliary high compression portion may have a different shape from the one side of the large-area high compression portion.

The invention according to claim 5 provides the absorbent article according to any one of claims 1 to 4, wherein the large-area high compression portion is arranged in contact with side walls of the compressed groove, or is arranged separately from the side walls of the compressed groove through the low compression portion.

In the invention according to claim 5, the other side, in the longitudinal direction of the absorbent article, of the large-area high compression portion may be arranged in contact with the side walls of the compressed groove or may be arranged separately from the side walls of the compressed groove.

The invention according to claim 6 provides the absorbent article according to any one of claims 1 to 5, wherein the large-area high compression portion includes one or more large-area high compression portions arranged at one intermediate position or at one end position of the compressed groove, or arranged both at intermediate and end positions of or only at intermediate positions of the compressed groove while spaced at larger intervals than arrangement intervals of the regularly-arranged high compression portions.

In the invention according to claim 6, with regard to an arrangement pattern, one or more large-area high compression portions may be arranged in the compressed groove. The arrangement pattern may be determined as desired, depending on the function or the size of the absorbent article.

Effects of the Invention

According to the invention as described above, it becomes possible to prevent a high compression portion from being defectively formed and also prevent a top sheet from being torn.

MODE FOR CARRYING OUT THE INVENTION

In the following, embodiments of the present invention are described below with reference to the accompanying drawings.

[Basic Structure of Sanitary Napkin 1]

Figure 1:
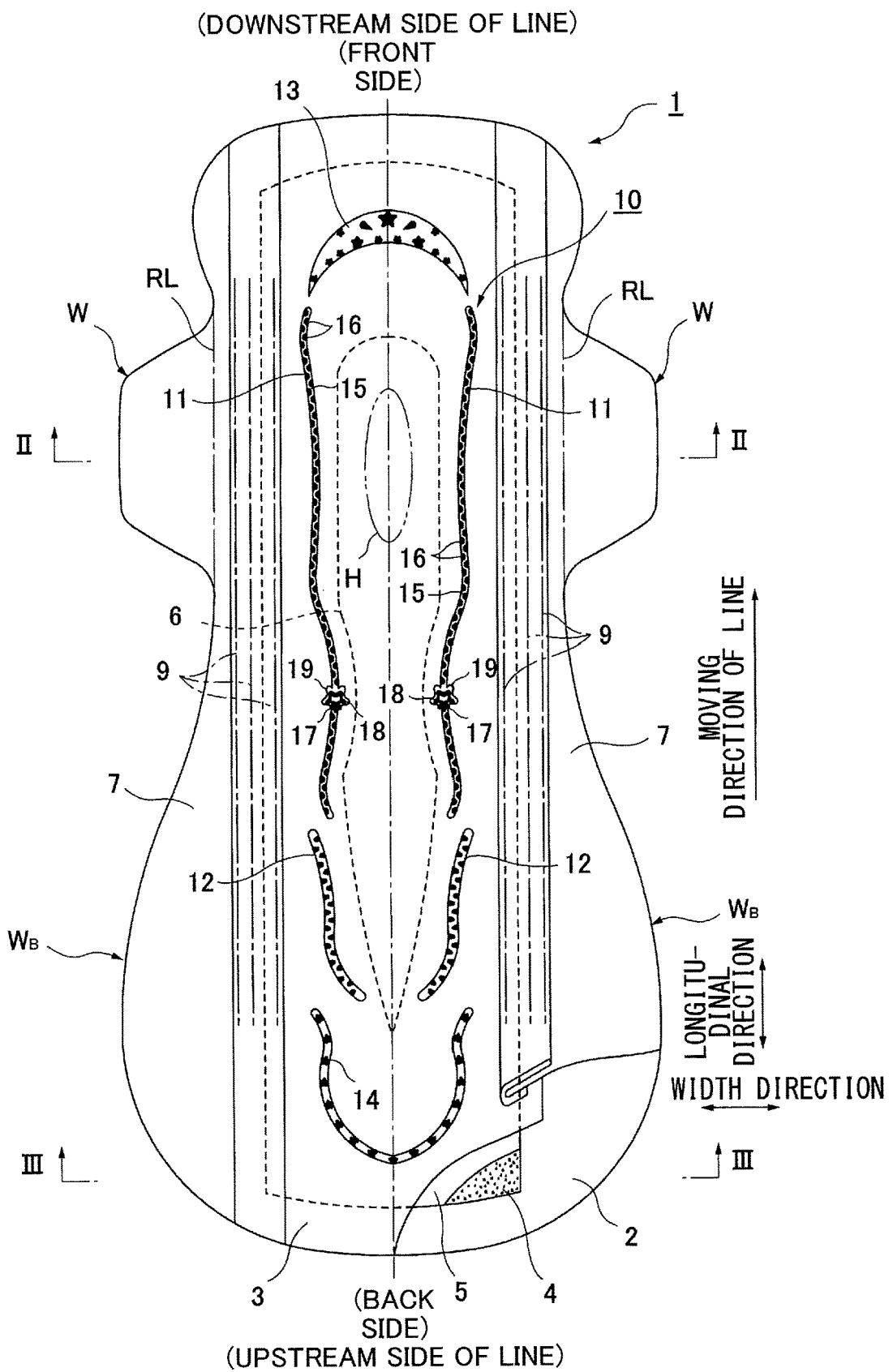
FIG. 1 is a partially expanded cutaway view of a sanitary napkin 1.
Figure 2:
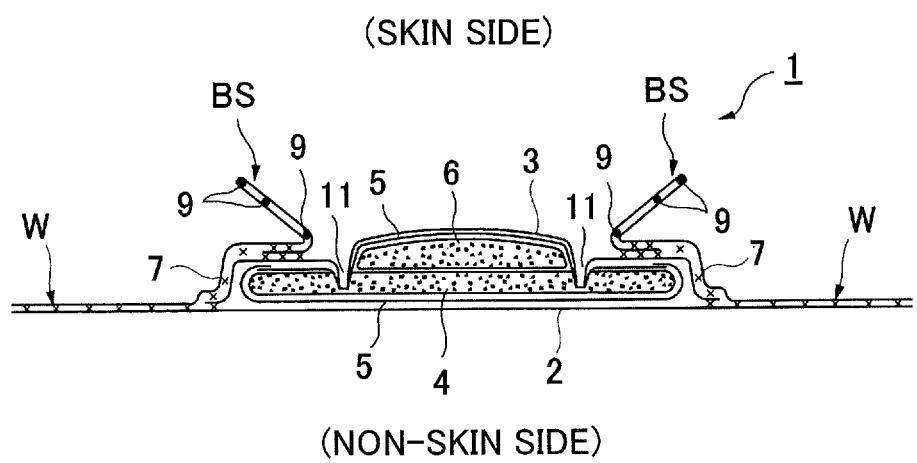
FIG. 2 is a cross-sectional view taken along a line II-II of FIG. 1.
Figure 3:
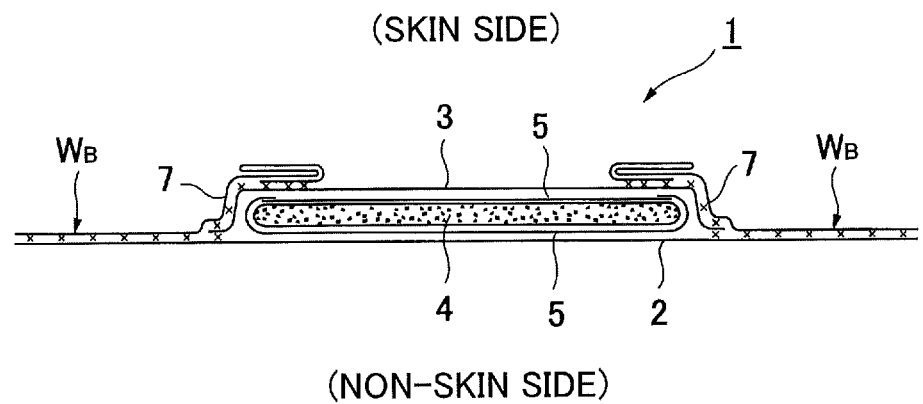
FIG. 3 is a cross-sectional view taken along a line III-III of FIG. 1.
Figure 4:
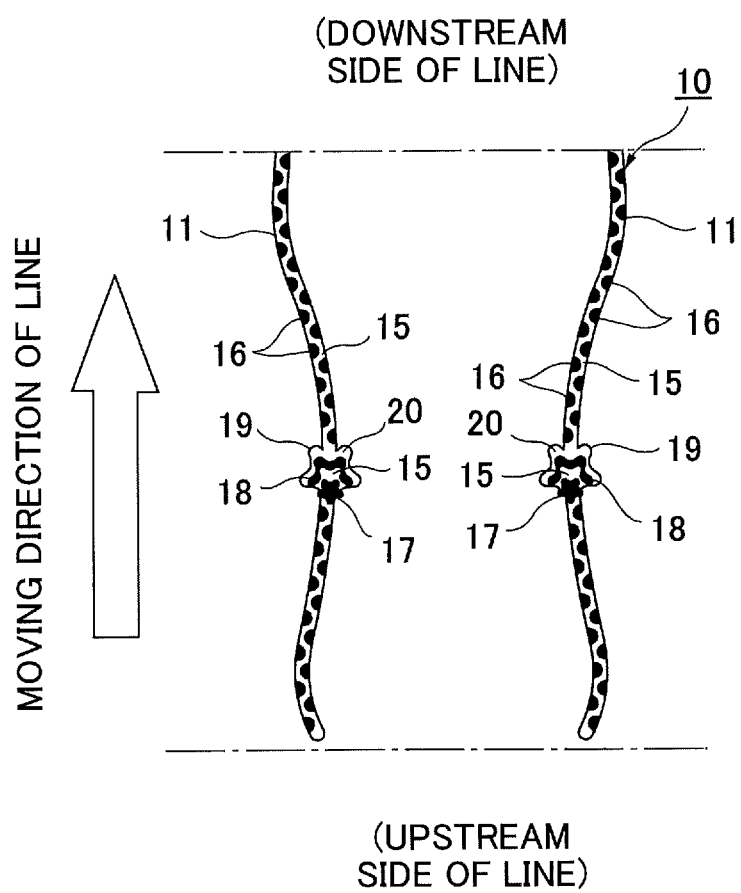
FIG. 4 is an enlarged view of a main portion of FIG. 1.

As illustrated in FIGS. 1 through 3, a sanitary napkin 1 according to the present invention includes: a liquid impermeable back sheet 2 formed of a polyethylene sheet, for example; a liquid permeable top sheet 3 that allows menstrual blood, vaginal discharge, and the like (hereinafter also collectively referred to as body fluids) to quickly pass through; an absorbent body 4 interposed between the sheets 2 and 3 and made of cotton-like pulp or synthetic pulp, for example; and a side non-woven fabric 7 provided over the approximately entire length of each side of a skin contact surface along a longitudinal direction. At front and back end portions of the absorbent body 4, outer end portions of the liquid impermeable back sheet 2 and the liquid permeable top sheet 3 are bonded to each other with an adhesive such as a hot-melt adhesive or with an adhesive means such as a heat seal or an ultrasonic seal. Furthermore, at each side of the absorbent body 4, the liquid impermeable back sheet 2 and the side non-woven fabric 7 that laterally extends longer than the absorbent body 4 are bonded to each other with an adhesive such as a hot-melt adhesive or with an adhesive means such as a heat seal and an ultrasonic seal. As a result, flaps without the absorbent body are formed. In the illustrated example, in order to maintain the shape of the absorbent body 4 and to improve diffusivity thereof, the absorbent body 4 is surrounded by an encapsulating sheet 5 made of a crepe paper sheet or a non-woven fabric; however, the encapsulating sheet 5 is not necessarily provided. Although not illustrated, a second sheet formed of a hydrophilic non-woven fabric and having approximately the same shape as the liquid permeable top sheet 3 may be disposed facing a non-skin side of the liquid permeable top sheet 3.

In the following, the structure of the sanitary napkin 1 will be described in more detail. The liquid impermeable back sheet 2 uses a sheet material such as polyethylene having at least a water shielding property. In addition, in terms of stuffiness prevention, a material having moisture permeability is preferably used. As such a water shielding and permeable sheet material, a microporous sheet is preferably used. The microporous sheet is obtained by forming a sheet by melting and kneading inorganic filler with olefin resin such as polyethylene and polypropylene, and subsequently stretching the sheet in one axial direction or two axial directions. On a non-skin side (an outer surface) of the liquid impermeable back sheet 2, one or more adhesive layers (not illustrated) are formed along the longitudinal direction of the napkin such that the sanitary napkin 1 is fixed to underwear when worn. As the liquid impermeable back sheet 2, a polyethylene laminate non-woven fabric having a plastic film and a non-woven fabric layered on each other may be used.

Next, as the liquid permeable top sheet 3, a perforated or an imperforated non-woven fabric, a porous plastic sheet, or the like is preferably used. Examples of a material fiber forming the non-woven fabric include synthetic fibers such as an olefin-based synthetic fiber such as polyethylene or polypropylene, a polyester-based synthetic fiber, and a polyamide-based synthetic fiber, regenerated fibers such as rayon and cuprammonium rayon, and natural fibers such as cotton. Further, as the liquid permeable top sheet 3, a non-woven fabric obtained by applying an appropriate processing method such as a spunlace method, a spunbond method, a thermal bond method, a melt blown method, or a needle punch method to any of the above-described material fibers may be used. Among these processing methods, the spunlace method is superior in terms of flexibility, the spunbond method is superior in terms of drape properties, and the thermal bond method is superior in terms of bulkiness and compression restorability. When a number of through-holes are formed on the liquid permeable top sheet 3, body fluids can become quickly absorbed, providing a wearer with an excellent dry touch. Although either a long fiber or a short fiber may be used as the non-woven fabric, it is preferable to use a short fiber in order to provide texture of towel cloth. Further, in order to facilitate an embossing process, an olefin-based fiber such as polyethylene or polypropylene having a relatively low melting point may be used. Further, a composite fiber such as a core-in-sheath fiber having a high-melting-point fiber as a core and a low-melting-point fiber as a sheath, a side-by-side fiber, or a split fiber may be preferably used.

The absorbent body 4 interposed between the liquid impermeable back sheet 2 and the liquid permeable top sheet 3 is formed of, for example, cotton-like pulp and a water-absorptive polymer. The water-absorptive polymer is mixed, for example, as a granular powder, into the pulp that forms the absorbent body. Examples of the pulp include chemical pulp made from wood, cellulose fibers such as dissolving pulp, and synthetic cellulose fibers such as rayon and acetate. In terms of function and price, softwood pulp with a long fiber length is more preferably used than hardwood pulp.

Further, a synthetic fiber may be mixed into the absorbent body 4. Examples of the synthetic fiber that may be used include polyolefin-based fibers such as polyethylene and polypropylene, polyester-based fibers such as polyethylene terephthalate and polybutylene terephthalate, polyamide-based fibers such as nylon, and a copolymer thereof. Also, a mixture of two types of the above-described fibers may be used. Further, a composite fiber such as a core-in-sheath fiber having a high-melting-point fiber as a core and a low-melting-point fiber as a sheath, a side-by-side fiber, or a split fiber may be used. Also, a mixture of two types of the above-described fibers may be used. Further, a composite fiber such as a core-in-sheath fiber having a high-melting-point fiber as a core and a low-melting-point fiber as a sheath, a side-by-side fiber, or a split fiber may be used. In order to have hydrophilicity with body fluids, the synthetic fiber preferably undergoes surface treatment by using, for example, a hydrophilizing agent when a hydrophobic fiber is used.

As illustrated in FIG. 1 and FIG. 2, a raised center portion 6 having an increased thickness toward the skin side is preferably provided in an area including a region corresponding to a body fluid discharge portion H of the absorbent body 4. The raised center portion 6 is located at a skin-side surface of the absorbent body 4, and is provided at a center portion in the width direction of the absorbent body 4. The raised center portion 6 has a width dimension and a longitudinal dimension smaller relative to those of the absorbent body 4. If the raised center portion 6 is too thick, stiffness increases and the raised center portion 6 does not well fit the body. If the raised center portion 6 is too thin, the raised center portion 6 does not sufficiently make close contact with the body fluid discharge portion H. Accordingly, the thickness of the raised center portion 6 is 3 to 25 mm, and is preferably 5 to 18 mm.

The raised center portion 6 is provided in an area including the region corresponding to at least the body fluid discharge portion H of the wearer. The raised center portion 6 may be formed into an elongated shape that continues from the area including the region corresponding to the body fluid discharge portion H to an area including a region corresponding to the intergluteal cleft of the wearer. Alternatively, the raised center portion 6 may be disposed only in the area including the region corresponding to the body fluid discharge portion H, and is not necessarily provided in the backward area including the region corresponding to the intergluteal cleft.

When the raised center portion 6 is formed into the elongated shape, which continues from the area including the region corresponding to the body fluid discharge portion H to the area including the region corresponding to the intergluteal cleft, a narrow width portion, whose outline on each side is curved inward in the width direction, is preferably provided at the back of the region corresponding to the body fluid discharge portion H. By providing the narrow width portion, the raised center portion 6 tends to fit a small recess or projection formed on the skin surface extending from the back end of the body fluid discharge portion H to the start position of the intergluteal cleft of the wearer, thereby enhancing close contact with the skin surface.

The raised center portion 6 includes at least a pulp fiber and a synthetic fiber. The pulp fiber and synthetic fiber are mixed at a ratio ranging from 80:20 to 20:80 in terms of weight, and are preferably mixed at a ratio ranging from 40:60 to 60:40 in terms of weight. Further, the raised center portion 6 may also include a water-absorptive polymer. Examples of the water-absorptive polymer include a polyacrylate cross-linked product, a self-crosslinked polyacrylic acid salt, an acrylic acid ester-vinyl acetate copolymer cross-linked saponified product, an isobutylene-maleic anhydride copolymer cross-linked product, a polysulfone salt cross-linked product, and a product obtained by partially cross-linking a water-swellable polymer such as polyethylene oxide or polyacrylamide. Among them, an acrylic acid or an acrylic acid salt, which is excellent in absorbed amount and water absorption rate, is preferable. For such a water-absorptive polymer having the above-described water absorption performance, it is possible to adjust the absorption power and the water absorption rate by adjusting the cross-linking density and the cross-linking density gradient in a production process. Because the raised center portion 6 promotes permeation into the absorbent body 4, what is known as gel blocking occurs when the content of the water-absorptive polymer is large. Thus, the content of the water-absorptive polymer in terms of weight is preferably 1% to 10% of the total weight of the pulp fiber and the synthetic fiber. When the content of the water-absorptive polymer exceeds 50%, the fibers become not entangled, decreasing the strength of the sheet and causing the sheet to be ripped or cracked. Thus, the water-absorptive polymer content of more than 50% is not desired.

As illustrated in the cross-sectional views of FIG. 2 and FIG. 3, a width dimension of the liquid permeable top sheet 3 is slightly larger than a width of the absorbent body 4 so as to cover the absorbent body 4. The side non-woven fabric 7, formed of a different material from the liquid permeable top sheet 3, is provided outside the liquid permeable top sheet 3. To be more specific, the side non-woven fabric 7 is formed of a non-woven fabric material to which appropriate water-repellency treatment or hydrophilic treatment is applied, depending on the purpose such as preventing menstrual blood or vaginal discharge from permeating or enhancing texture. As the side non-woven fabric 7, a sheet that uses a synthetic fiber or a regenerated fiber as a material and is formed by an appropriate processing method may be used. Preferably, in order to prevent stuffiness while eliminating friction with the skin, a non-woven fabric having air permeability with a reduced basis weight may be used as the side non-woven fabric 7. Preferably, in order to prevent stuffiness while eliminating friction with the skin, a non-woven fabric having air permeability with a reduced basis weight may be used as the side non-woven fabric 7. To be more specific, a non-woven fabric with a basis weight of 13 to 23 g/m$^2$ is desirably used. Further, in order to securely prevent body fluids from permeating, a water-repellent non-woven fabric coated with a silicon-based, a paraffin-based, or an alkyl-chromic-chloride-based water-repellent agent is preferably used.

As illustrated in FIG. 2 and FIG. 3, on each outer side of the sanitary napkin relative to the middle portion in the width direction, the side non-woven fabric 7 is bonded from an inward position to an outer edge of the liquid impermeable back sheet 2 with an adhesive such as a hot-melt adhesive. The layered sheet portions of the liquid impermeable back sheet 2 and each of the side non-woven fabrics 7 form flaps on both sides of the absorbent body 4, without the absorbent body 4 being interposed. The flaps may include a pair of right and left wing-shaped flaps W, W at positions alongside the body fluid discharge region H of the absorbent body 4, and may also include hip-holding flaps WB, WB on the buttocks side (back side) relative to the wing-shaped flaps W, W. Outer surfaces of the wing-shaped flaps W, W and the hip-holding flaps WB, WB have adhesive layers (not illustrated). When the sanitary napkin is attached to underwear, the wing-shaped flaps W, W are folded back at positions of fold-back lines RL so as to be fixed to a crotch portion of the underwear, and also the hip-holding flaps WB, WB are fixed to an inner surface of the underwear.

An inner side of the side non-woven fabric 7 is folded back to be almost two-fold, and one or a plurality of (in the illustrated example, three) threadlike elastic expansion and contraction members 9, 9 are provided inside this double sheet. The ends or appropriate positions in the longitudinal direction of each of the elastic expansion and contraction members 9, 9 are fixed at a middle portion in the height direction of the double sheet. In a layered state in which the double sheet is folded outward once, the front and back ends of the double sheet is bonded to the absorbent body 4 side as illustrated in FIG. 3. Accordingly, right and left three-dimensional linear gathers BS, BS standing toward the skin side while being sloped outward are formed as illustrated in FIG. 2.

[Compressed Grooves]

In the sanitary napkin 1, a compressed groove 10 that is recessed from a skin contact surface side (an outer surface side of the liquid permeable top sheet 3) toward a non-skin side (a liquid impermeable back sheet 2 side) is formed. As illustrated in FIG. 1, the compressed groove 10 has front-side lengthwise compressed grooves 11, 11 that are continuously formed, in the approximately longitudinal direction of the sanitary napkin 1, on each side extending from the area including the region corresponding to the body fluid discharge portion H to the area including the region corresponding to the intergluteal cleft. The compressed groove 10 also includes back-side lengthwise compressed grooves 12, 12 that are formed at the back away from the front-side lengthwise compressed grooves 11 and are formed on each side of a region corresponding to the back end of the intergluteal cleft. The compressed groove 10 also has a front-end crescent-shaped compressed groove 13 that is provided at the front away from the front-side lengthwise compressed grooves 11, 11, crosses the center line in the longitudinal direction of the sanitary napkin 1, and is formed approximately along the width direction of the sanitary napkin 1. The compressed groove 10 also has a back-end curved compressed groove 14 that is provided at the back away from the back-side lengthwise compressed grooves 12, 12, crosses the center line in the longitudinal direction of the sanitary napkin 1, and is curved backward.

A low compression portion 15 and a predetermined high compression portion are formed on the bottom surface of the compressed groove 10. The low compression portion 15 is a portion formed such that the depth of the groove is relatively small and density is low. The high compression portion is a portion formed such that the depth of the groove is relatively large and density is high.

In the sanitary napkin 1 according to the embodiment of FIG. 1, in each of the front-side lengthwise compressed grooves 11, the high compression portion includes regularly-arranged high compression portions 16 that are regularly arranged in the longitudinal direction of the compressed groove 11, a large-area high compression portion 17 that is irregularly arranged in the compressed groove 11 and has an area larger than an area of each of the regularly-arranged high compression portions 16, and an auxiliary high compression portion 18 that is arranged at one side (at the front side), in the longitudinal direction of the napkin, of the large-area high compression portion 17 through the low compression portion 15 and that is formed wider than the large-area high compression portion 17 so as to surround the one side, in the longitudinal direction of the napkin, of the large-area high compression portion 17.

In the present sanitary napkin 1, the large-area high compression portion 17 provided at a predetermined position of each of the compressed grooves 11 can serve as a base for transmitting pressure, which is exerted from the both sides in the width direction when the napkin is worn, to the center portion of the absorbent body. As a result, the center portion of the absorbent body can readily protrude toward the skin side. Also, the large-area high compression portion 17 serves as a distinctive feature, thereby improving external appearance of the compressed groove 10. To be more specific, when the sanitary napkin 1 is worn, pressure such as legs pressure or buttocks pressure is exerted inwardly from the both sides in the width direction. The compressed groove 10, provided on the both sides in the width direction, transmits such pressure to the center portion of the absorbent body. At this time, the large-area high compression portion 17 formed in the compressed groove 10 allows pressure, exerted inwardly in the width direction, to be concentrated in the large-area high compression portion 17. Accordingly, the large-area high compression portion 17 can serve as a base for causing the center portion of the absorbent body in the width direction to protrude toward the skin side. By causing the center portion to protrude toward the skin side, the fit of the sanitary napkin can be improved.

The sanitary napkin 1 is manufactured by what is termed as a vertically moving line method in which the moving direction of the line is taken as the longitudinal direction of the sanitary napkin 1, one side (the front side) in the longitudinal direction of the sanitary napkin 1 is taken as the downstream side in the moving direction of the line during manufacturing, and the other side (the back side) in the longitudinal direction is taken as the upstream side in the moving direction of the line during manufacturing.

In order to form the compressed groove 10, the skin-side surface of the absorbent body 4 being covered by the liquid permeable top sheet 3 is passed between an embossing roll and an anvil roll, and is compressed by projections formed on the embossing roll.

At this time, when forming a high compression portion having a relatively large area, compression pressure may be dispersed due to the large area, thereby causing a high compression pattern to be unsuccessfully formed. Conversely, compression pressure may be concentrated in a part of the high compression portion, possibly resulting in an embossing defect such as a tear in the top sheet.

In light of the above, in the sanitary napkin 1, the auxiliary high compression portion 18 is arranged at the downstream side of the large-area high compression portion 17 and is formed wider than the large-area high compression portion 17 so as to surround the downstream side of the large-area high compression portion 17. Therefore, the large-area high compression portion 17 can be pressed while the absorbent body 4 including the top sheet 3 is being temporarily held by the auxiliary high compression portion 18. Accordingly, the large-area high compression portion 17 can be properly formed while also preventing the top sheet 3 from being torn. Thus, embossing defects will not readily occur. Further, because the large-area high compression portion 17 can be successfully formed without any defect, pressure from the both sides can be readily transmitted to the center portion of the absorbent body and the center portion can readily protrude toward the skin side, allowing the fit of the sanitary napkin to be improved.

The regularly-arranged high compression portions 16 are portions that are arranged at approximately equal intervals along the compressed groove 11. The regularly-arranged high compression portions 16 may be formed so as not to cross the compressed groove 11 in the width direction or may be formed so as to cross the compressed groove 11 in the width direction. The regularly-arranged high compression portions 16 are formed in a portion of the compressed groove 11 extending at approximately the same width.

The large-area high compression portion 17 has a relatively larger area than an area of each of the regularly-arranged high compression portions 16. The area of the large-area high compression portion 17 is 2 to 10 times larger, and is preferably 3 to 5 times larger than the area of each of the regularly-arranged high compression portions 16. By setting the area within this range, the large-area high compression portion 17 readily becomes a base for directing pressure inward in the width direction, and external appearance can also be improved.

Figure 5:
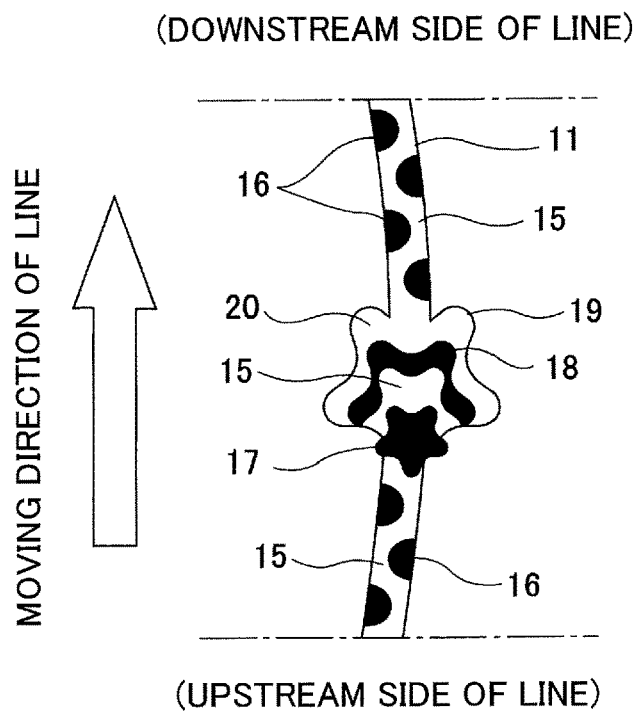
FIG. 5 is an enlarged view of a front-side lengthwise compressed groove 11.

Referring to FIG. 5, the large-area high compression portion 17 is preferably formed in a vastly enlarged portion 19 in which the width of the compressed groove 11 is vastly enlarged. The vastly enlarged portion 19 is a portion in which a distance between both side walls of the compressed groove 11 is vastly enlarged, and is formed continuously from the connected compressed groove 11 without being separated from the connected compressed groove 11. Further, the compressed groove 11 can be curved approximately at the same curvature before and after the vastly enlarged portion 19, without being separated or bent at the vastly enlarged portion 19 provided in the middle.

The regularly-arranged high compression portions 16 are not arranged in the vastly enlarged portion 19. The large-area high compression portion 17 and the auxiliary high compression portion 18 are provided in the vastly enlarged portion 19. Namely, the regularly-arranged high compression portions 16 are formed in the part of the compressed groove 11 that is connected to the vastly enlarged portion 19.

The large-area high compression portion 17 is preferably formed wider than the part of the compressed groove 11 that is connected to the vastly enlarged portion 19 and extends in the front-back direction of the napkin at approximately the same width. Accordingly, the large-area high compression portion 17 readily becomes a base for directing pressure, which is exerted from the both sides in the width direction, inward, and also external appearance can be improved.

The auxiliary high compression portion 18 is arranged at the downstream side of the large-area high compression portion 17 through the low compression portion 15. Namely, the auxiliary high compression portion 18 is not connected to the large-area high compression portion 17. By providing the low compression portion 15 between the auxiliary high compression portion 18 and the large-area high compression portion 17, the auxiliary high compression portion 18 is arranged separately from the large-area high compression portion 17. Namely, when a line passing through the large-area high compression portion 17 and extending in the longitudinal direction of the napkin is drawn, the auxiliary high compression portion 18, the low compression portion 15, and the large-area high compression portion 17 are arranged in this order from the downstream side toward the upstream side. Thus, when the sanitary napkin 1 is pressed by the embossing roll in the manufacturing process, the auxiliary high compression portion 18, the low compression portion 15, and the large-area high compression portion 17 are pressed in this order.

The auxiliary high compression portion 18 is formed wider than the large-area high compression portion 17 so as to surround the downstream side of the large-area high compression portion 17. Namely, when the large-area high compression portion 17 is projected onto the downstream side (front side) along the longitudinal direction of the napkin, the projected large-area high compression portion 17 inevitably passes through the auxiliary high compression portion 18.

The auxiliary high compression portion 18 is preferably formed in such a manner that an outer edge of the upstream side of the auxiliary high compression portion 18 overlaps a part of or the entirety of the large-area high compression portion 17 in the width direction of the napkin. Accordingly, the downstream side of the large-area high compression portion 17 is completely surrounded by the auxiliary high compression portion 18. Thus, an effect obtained by forming the auxiliary high compression portion 18 can be exhibited with more certainty.

The auxiliary high compression portion 18 is preferably formed into a linear shape or a band shape extending approximately along the width direction of the napkin, so as to surround the downstream side of the large-area high compression portion 17. The line width or the band width of the auxiliary high compression portion 18 is preferably smaller than the size (the maximum dimension such as the width dimension or the longitudinal dimension in planar view) of the large-area high compression portion 17. Accordingly, in the embossing processing, the large-area high compression portion 17 can be compressed while being temporarily held by the auxiliary high compression portion 18 having a smaller area than that of the large-area high compression portion 17.

As illustrated in FIG. 5, in the vastly enlarged portion 19, an auxiliary low compression portion 20 wider than the auxiliary high compression portion 18 is preferably provided at the downstream side of the auxiliary high compression portion 18 so as to surround the downstream side of the auxiliary high compression portion 18. Further, by providing the auxiliary low compression portion 20 at the downstream side of the auxiliary high compression portion 18, while the absorbent body 4 including the top sheet 3 is being temporarily held with pressure lower than that for the auxiliary high compression portion 18, the auxiliary high compression portion 18 and the large-area high compression portion 17 can be pressed. Therefore, embossing defects caused by pressing the auxiliary high compression portion 18 and the large-area high compression portion 17 can be further reduced. The auxiliary low compression portion 20 is disposed adjacent to the auxiliary high compression portion 18, and extends from the outer edge of the auxiliary high compression portion 18 to the outer edge of the vastly enlarged portion 19. The auxiliary low compression portion 20 is preferably formed in such a manner that an outer edge of the upstream side of the auxiliary low compression portion 20 overlaps a part of or the entirety of the auxiliary high compression portion 18 in the width direction of the napkin. Accordingly, the downstream side of the auxiliary high compression portion 18 is completely surrounded by the auxiliary low compression portion 20. Thus, an effect obtained by forming the auxiliary low compression portion 20 can be exhibited with more certainty. When a line passing through the large-area high compression portion 17 and extending in the longitudinal direction of the napkin is drawn in the vastly enlarged portion 19 provided with the auxiliary low compression portion 20, the auxiliary low compression portion 20, the auxiliary high compression portion 18, the low compression portion 15, and the large-area high compression portion 17 are arranged in this order from the downstream side toward the upstream side, in such a manner that low compression portions and high compression portions are alternately arranged. Thus, embossing defects can be prevented with more certainty.

Figure 6:
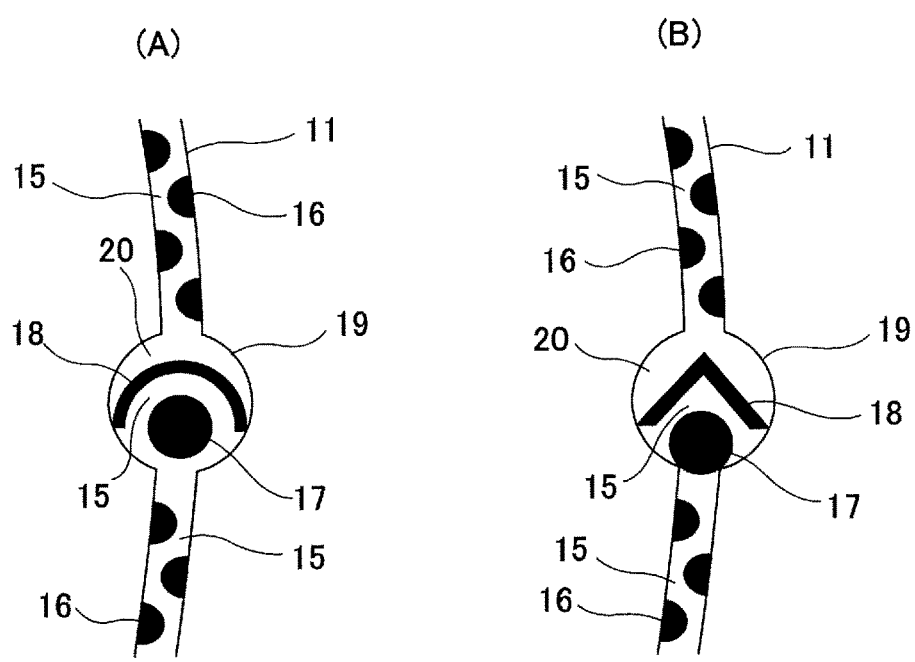
FIG. 6 is an enlarged view of a front-side lengthwise compressed groove 11 according to a variation.

In the example illustrated in FIG. 5, the large-area high compression portion 17 is formed into an approximately star shape in planar view. However, the large-area high compression portion 17 may be formed into a circular shape in planar view as illustrated in FIG. 6. Alternatively, the large-area high compression portion 17 may take various shapes such as an elliptical shape, a polygonal shape, a semicircular shape, and a drop shape, although not illustrated.

As illustrated in FIG. 5 and FIG. 6 (A), the auxiliary high compression portion 18 may be formed into approximately the same shape in planar view as that of the downstream side of the large-area high compression portion 17. Alternatively, the auxiliary high compression portion 18 may be formed into a different shape from that of the downstream side of the large-area high compression portion 17 as illustrated in FIG. 6 (B). When formed into a different shape, the auxiliary high compression portion 18 is preferably formed into a linear shape that widens from the center of the groove width at the downstream side toward the both sides at the upstream side as illustrated in FIG. 6 (B), so as to prevent embossing defects caused when the auxiliary high compression portion 17 is pressed.

Also, as illustrated in FIG. 5 and FIG. 6 (B), the large-area high compression portion 17 may be arranged in contact with side walls of the compressed groove 11 or side walls of the vastly enlarged portion 19. Alternatively, as illustrated in FIG. 6 (A), the large-area high compression portion 17 may be arranged separately from the side walls of the compressed groove 11 and the side walls of the vastly enlarged portion 19 through the low compression portion 15. In the former case, the large-area high compression portion 17 allows pressure exerted from the outside in the width direction to become readily transmitted to the inside. In the latter case, because the entire periphery of the large-area high compression portion 17 is surrounded by the low compression portion 15, it becomes possible to further reduce embossing defects while also improving appearance of the large-area high compression portion 17.

Figure 7:
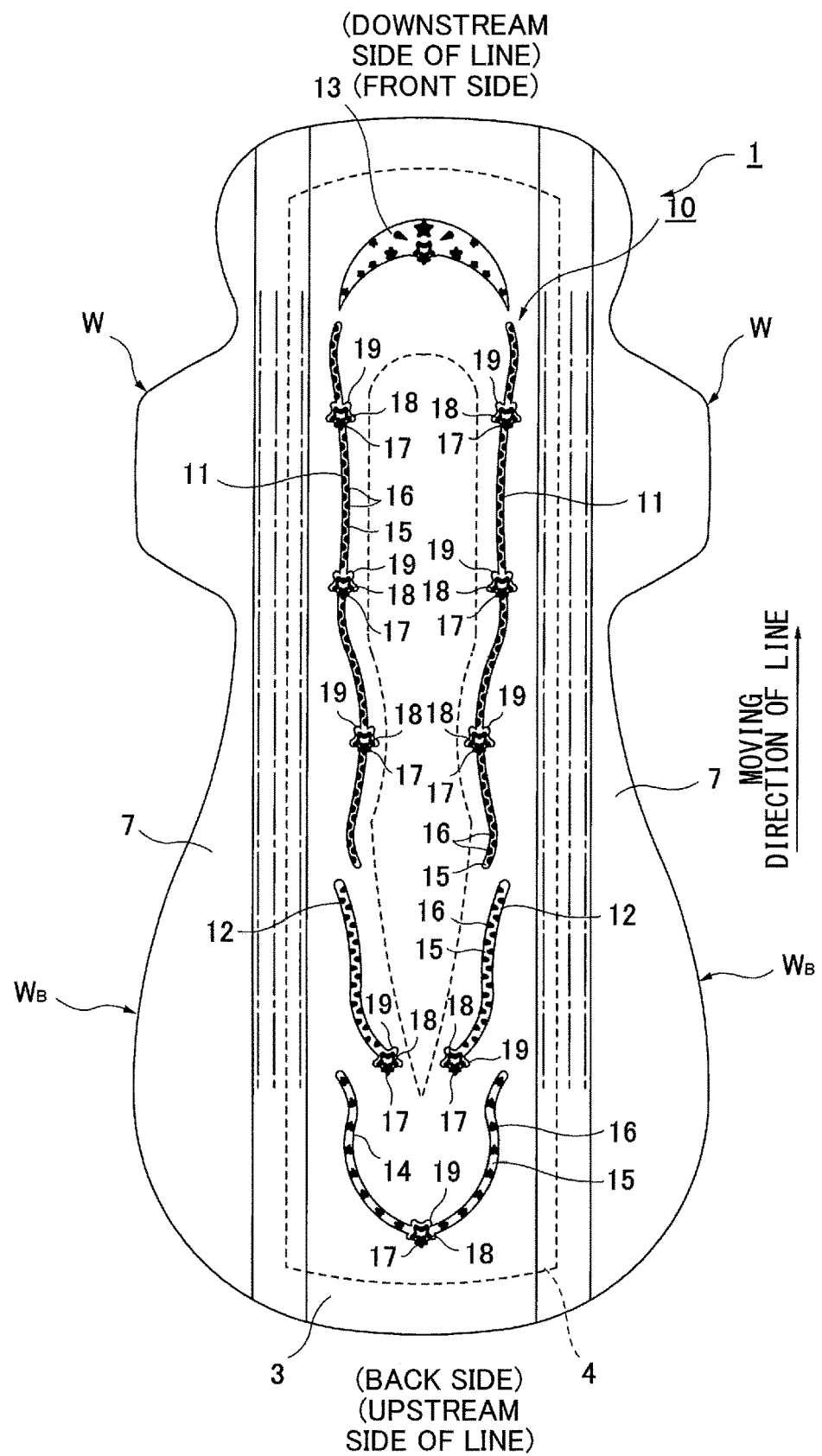
FIG. 7 is an expanded view of a sanitary napkin 1 according to the variation.

In the sanitary napkin 1 illustrated in FIG. 1, only one large-area high compression portion 17 is provided at an intermediate position of each of the front-side lengthwise compressed grooves 11. However, as illustrated in FIG. 7, a plurality of large-area high compression portions 17 may be provided at any positions of the compressed grooves 11 through 14. FIG. 7 illustrates exemplary arrangement of the large-area high compression portions 17. Only some of the large-area high compression portions 17 illustrated in FIG. 7 may be arranged, or the large-area high compression portions 17 may be arranged at other positions. To be more specific, the large-area high compression portions 17 may be provided at one intermediate position or at one end position of each of the compressed grooves 11 through 14. Alternatively, the large-area high compression portions 17 may be arranged at a plurality of positions both at intermediate and end positions of or only at intermediate positions of each of the compressed grooves 11 through 14 while spaced at larger intervals than arrangement intervals of the regularly-arranged high compression portions 16.

In the example of FIG. 7, three large-area high compression portions 17 are arranged in an intermediate portion of each of the front-side lengthwise compressed grooves 11 while being spaced apart from each other in the longitudinal direction of the groove. Also, one large-area high compression portion 17 is arranged at a rear end position of each of the back-side lengthwise compressed grooves 12, one large-area high compression portion 17 is arranged at a rear edge position in the middle of the front-end crescent-shaped compressed groove 13 in the width direction, and one large-area high compression portion 17 is arranged at a middle position of the back-end curved compressed groove 14 in the width direction. When the large-area high compression portions 17 are provided at a plurality of positions of a compressed groove, the large-area high compression portions 17 make it easier to transmit pressure to the inside in the width direction. Also, when the large-area high compression portions 17 are provided at an end of compressed grooves, stiffness at the end of the compressed grooves can be prevented from decreasing. Further, when the large-area high compression portions 17 are provided at middle positions of transverse compressed grooves in the width direction, the large-area high compression portions 17 serve as distinctive features, and thus, external appearance of the compressed groove can be improved.

Other Embodiment

In the above-described embodiment, the front side of the sanitary napkin 1 is regarded as the downstream side and the back side is regarded as the upstream side. Conversely, the back side of the sanitary napkin 1 may be regarded as the downstream side, and the front side may be regarded as the upstream side.

DESCRIPTION OF THE REFERENCE NUMERAL

1 sanitary napkin
2 liquid impermeable back sheet
3 liquid permeable top sheet
4 absorbent body
5 encapsulating sheet
6 raised center portion
7 side non-woven fabric
9 threadlike elastic expansion and contraction member
10 compressed groove
11 front-side lengthwise compressed groove
12 back-side lengthwise compressed groove
13 front-end crescent-shaped compressed groove
14 back-end curved compressed groove
15 low compression portion
16 regularly-arranged high compression portion
17 large-area high compression portion
18 auxiliary high compression portion
19 vastly enlarged portion
20 auxiliary low compression portion

The invention claimed is:

1. An absorbent article comprising,
an absorbent body interposed between a liquid permeable top sheet and a liquid impermeable back sheet, a low compression portion and a high compression portion being formed on a bottom surface of a compressed groove that is recessed from a skin contact surface side,
wherein the high compression portion includes regularly-arranged high compression portions that are regularly arranged in a longitudinal direction of the compressed groove, a large-area high compression portion that is arranged in the compressed groove and has a star shape larger than an area of each of the regularly-arranged high compression portions, and an auxiliary high compression portion that is arranged only on a side of the large-area high compression portion that faces a region corresponding to a body fluid discharge portion of a user of the absorbent article, only one auxiliary high compression portion being provided to one large-area high compression portion,
wherein the auxiliary high compression portion has a shape that conforms to a contour of the star shape of the large-area high compression portion,
wherein the auxiliary high compression portion at least partially overlaps the large-area high compression portion in a longitudinal direction of the absorbent article,
wherein the compressed groove has an enlarged portion that has an enlarged width and the large-area high compression portion and the auxiliary high compression portion are formed in the enlarged portion, and
wherein the enlarged portion has a shape that is substantially the same as the star shape of the large-area high compression portion.

2. The absorbent article according to claim 1, wherein an auxiliary low compression portion that is wider than the auxiliary high compression portion is disposed so as to surround one side, in the longitudinal direction of the absorbent article, of the auxiliary high compression portion.

3. The absorbent article according to claim 1, wherein the large-area high compression portion is arranged in contact with side walls of the compressed groove, or is arranged separately from the side walls of the compressed groove through the low compression portion.

4. The absorbent article according to claim 1, wherein the large-area high compression portion includes one or more large-area high compression portions arranged at one intermediate position or at one end position of the compressed groove, or arranged both at intermediate and end positions of or only at intermediate positions of the compressed groove while spaced at larger intervals than arrangement intervals of the regularly-arranged high compression portions.

5. The absorbent article according to claim 1, wherein the large-area high compression portion has only one large-area high compression portion in the compressed groove, and the only one large-area high compression portion is arranged at one intermediate position or at one end position of the compressed groove.

6. The absorbent article according to claim 1, wherein one of the regularly-arranged high compression portions is arranged next to the large-area high compression portion without the auxiliary high compression portion between the large-area high compression portion and the one of the regularly-arranged high compression portions on a side of the large-area high compression portion that is opposite to the side where the auxiliary high compression portion is provided.

7. The absorbent article according to claim 1, wherein the compressed groove includes a first inner side wall and a second inner side wall that is parallel to the first inner side wall with a gap, and the regularly-arranged high compression portions are provided on the first inner side wall and the second inner side wall, alternately along the longitudinal direction of the compressed groove.

* * * * *